(12) United States Patent
Daane

(10) Patent No.: US 7,660,625 B2
(45) Date of Patent: Feb. 9, 2010

(54) CATHETER WITH COMPACTLY TERMINATED ELECTRONIC COMPONENT

(75) Inventor: Laurence A. Daane, Portland, OR (US)

(73) Assignee: Tyco Electronics Corporation, Middletown, PA (US)

( * ) Notice: Subject to any disclaimer, the term of this patent is extended or adjusted under 35 U.S.C. 154(b) by 411 days.

(21) Appl. No.: 11/128,082

(22) Filed: May 12, 2005

(65) Prior Publication Data

US 2006/0258937 A1 Nov. 16, 2006

(51) Int. Cl.
*A61B 5/05* (2006.01)
(52) U.S. Cl. ........................................ 600/424; 600/420
(58) Field of Classification Search ................ 600/414, 600/422, 426
See application file for complete search history.

(56) References Cited

U.S. PATENT DOCUMENTS

| | | | |
|---|---|---|---|
| 5,050,601 A * | 9/1991 | Kupersmith et al. ........... 607/5 |
| 5,344,435 A | 9/1994 | Turner et al. | |
| 5,776,176 A | 7/1998 | Rudie et al. | |
| 5,810,803 A | 9/1998 | Moss et al. | |
| 5,964,705 A | 10/1999 | Truwit et al. | |
| 6,304,769 B1 * | 10/2001 | Arenson et al. ............. 600/424 |
| 2002/0139561 A1 * | 10/2002 | Buck et al. .............. 174/113 R |
| 2004/0024308 A1 * | 2/2004 | Wickline et al. ............ 600/422 |
| 2004/0116800 A1 * | 6/2004 | Helfer et al. ................ 600/411 |
| 2004/0171934 A1 * | 9/2004 | Khan et al. ................. 600/435 |

OTHER PUBLICATIONS

International Search Report for International Application No. PCT/US2006/018438, mailed Oct. 6, 2006.

* cited by examiner

*Primary Examiner*—Carl H. Layno
*Assistant Examiner*—Jon-Eric C. Morales

(57) ABSTRACT

A cable assembly includes an elongated catheter defining a lumen. A cable within the lumen has at least first and second electrically independent conductors. A first electrical component is connected to the catheter and has a first lead and second lead. The first lead is connected to the first conductor at a first connection, and the second lead connected to the second conductor at a second connection. The first and second connections are spaced apart along the length of the catheter, and the component is positioned at an intermediate location between the first and second connections. The component may be a coil, with leads extending in opposite directions, and only one of the conductors may pass through the coil. The assembly may include multiple components spaced apart along the length of the catheter.

17 Claims, 2 Drawing Sheets

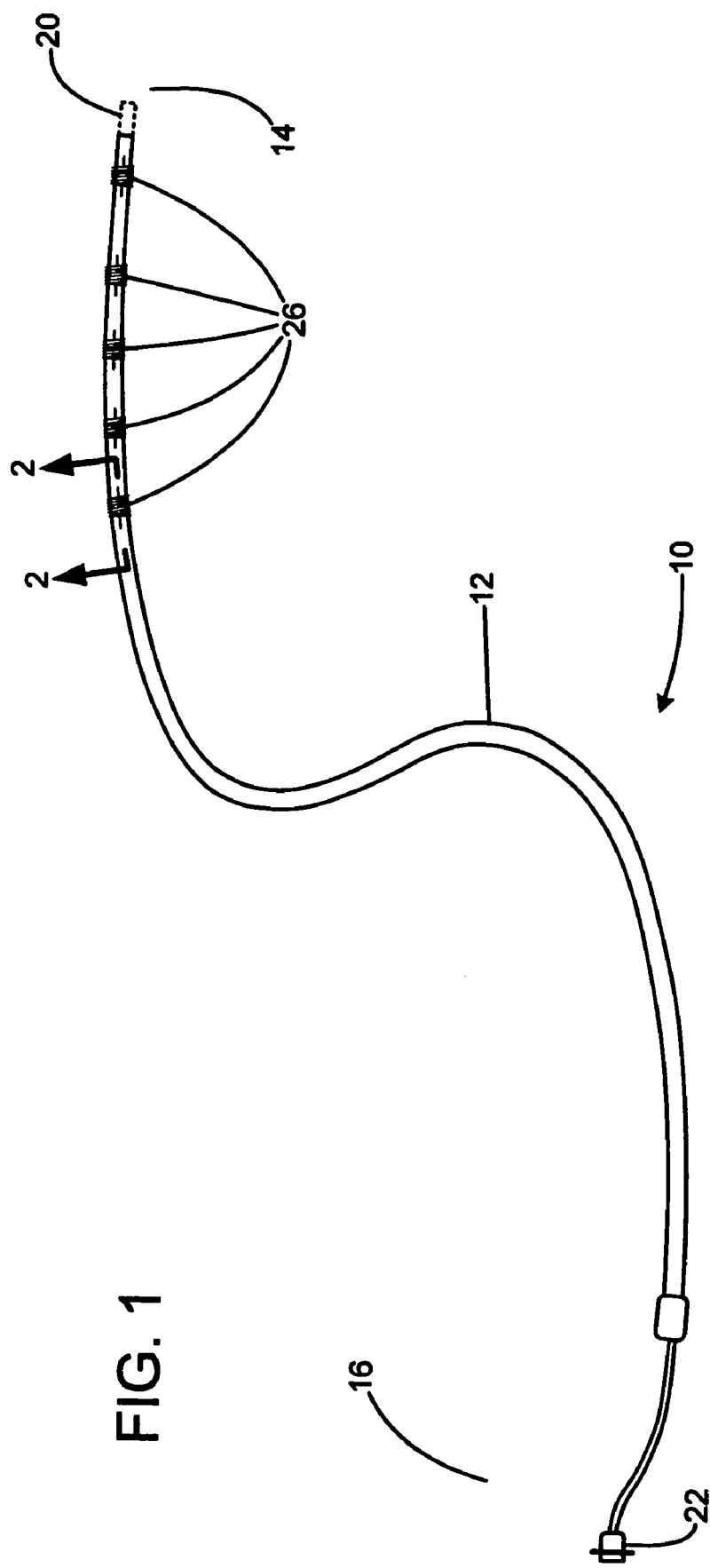

CATHETER WITH COMPACTLY TERMINATED ELECTRONIC COMPONENT

BACKGROUND OF THE INVENTION

1. Field of the Invention

This invention relates to electronic cables for catheterized medical applications.

2. Introduction to the Invention

Medical instruments employ catheters for a wide range of uses, including imaging, sensing, and treatment of internal tissue. For instance, catheters are inserted into a patient's blood vessels, such as to reach the heart for imaging or therapeutic action. Catheters have one or more lumens or bores that extend the length of the catheter, and through which wires or other implements pass. These may include mechanical guide wires used to bend and steer the catheter for insertion, fiber optic or current carrying wires used to provide a light source, and signal wires used to carry images or other sensing signals.

Catheters used during imaging procedures such as by Magnetic Resonance Imaging (MRI) may employ components able to provide a detectable reference point in space, so that the MRI software can locate the catheter, aiding its navigation to a desired location via a desired path. Such elements may employ a series of coils that each wraps closely about the exterior of the catheter at intervals along the length of the catheter near the free end. These coils may also be covered with thin layers of other materials to help seal the catheter, make the surface smoother, or affect the flexibility of the catheter region containing the coils. However, the conventional approaches employed to connect these coils to wires extending to instrumentation are bulky, creating significant lumps that limit the vessels in which the catheter may be inserted, or which require more internal space and thus limit the catheter's capacity to host other needed lumens for other functions.

Accordingly, there is a need for a catheter with compact interconnections to the components employed.

BRIEF SUMMARY OF THE INVENTION

The present invention overcomes the limitations of the prior art by providing a cable assembly including an elongated catheter defining a lumen. A cable within the lumen has at least first and second electrically independent conductors. A first electrical component is connected to the catheter and has a first lead and second lead. The first lead is connected to the first conductor at a first connection, and the second lead connected to the second conductor at a second connection. The first and second connections are spaced apart along the length of the catheter, and the component is positioned at an intermediate location between the first and second connections. The component may be a coil, with leads extending in opposite directions, and only one of the conductors may pass through the coil. The assembly may include multiple components spaced apart along the length of the catheter.

BRIEF DESCRIPTION OF THE DRAWINGS

The invention is illustrated by the drawings in which FIG. 1 is a perspective view of a cable assembly according to a preferred embodiment of the invention.

DETAILED DESCRIPTION OF THE INVENTION

Figure 3:
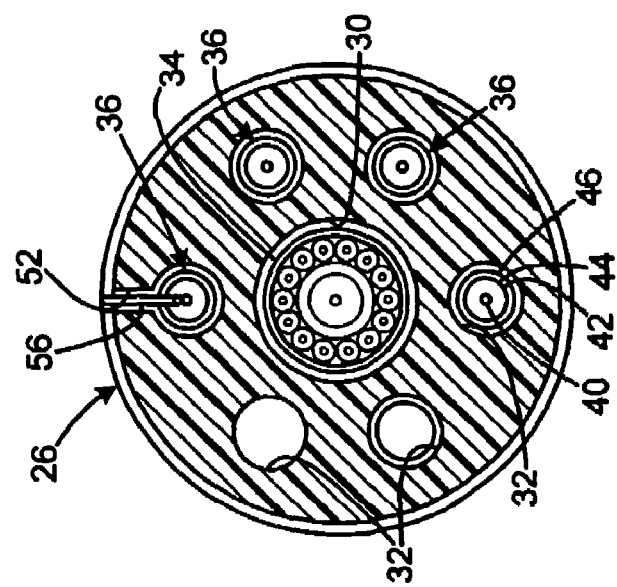
FIG. 3 is a lateral enlarged sectional view of the embodiment of FIG. 1 taken along line 3-3 of FIG. 2.

FIG. 1 shows a catheter assembly 10 having a flexible elongated catheter 12 with a free end 14, and a connection end 16. One or more transducers or other circuit components 20 is attached at the free end, and one or more connectors 22 is attached at the connection end. The free end circuit elements may be of any type used for internal medical procedures, whether sensing or therapeutic. These elements may be required for operation of an imaging device, a surgical tool of electrical or mechanical operation, a radiation source, or any other type of device. Alternately, catheters may contain one or more empty lumens to allow such free end elements to be fed down the length of the catheter for use as required to complete a specific medical procedure. The connectors provide electrical or other operational connection to instruments that operate the components and instruments on the catheter.

The catheter includes several closely-wound helical electromagnetic coils 26 that are positioned in an array near the free end of the catheter, spaced apart at intervals. The coils serve to assist in positioning the catheter during a procedure. An MRI system detects the magnetic fields generated by a current passing through each coil. The coils may thus be activated so that a surgeon can visualize the catheter location in relation to an intended insertion path in an MRI image.

Figure 2:
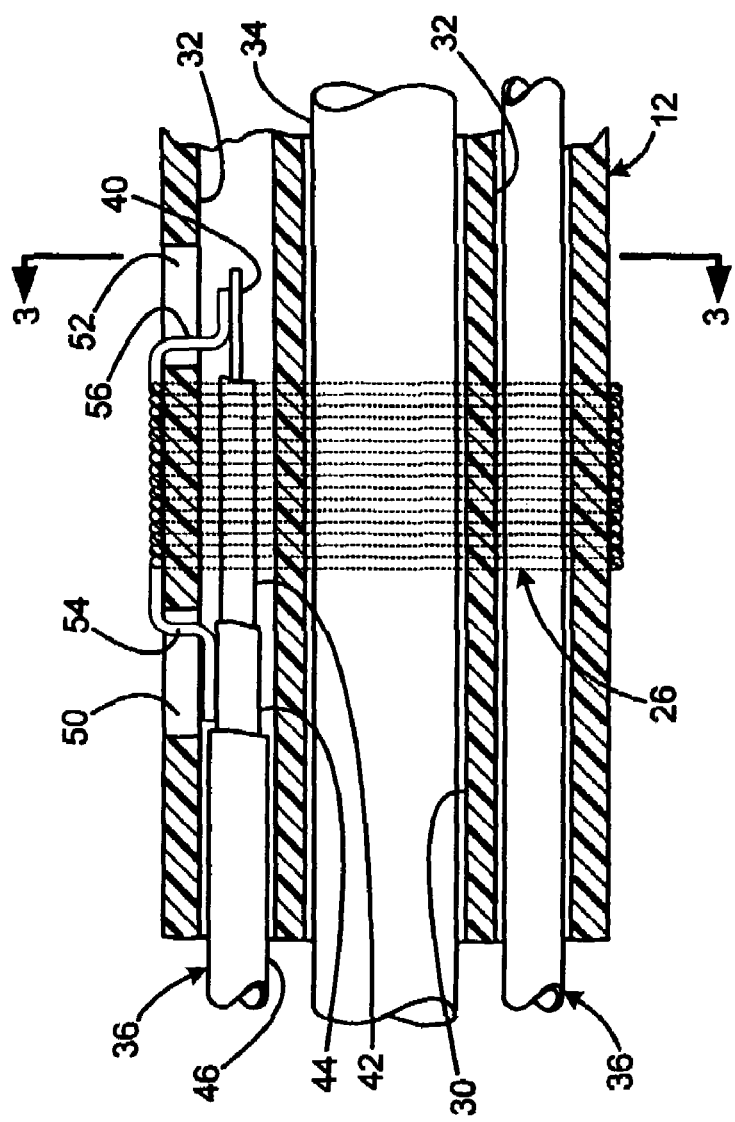
FIG. 2 is a lateral enlarged sectional view of the embodiment of FIG. 1 taken along line 2-2 of FIG. 1.

As shown in FIGS. 2 and 3, in a preferred embodiment, the catheter defines a number of hollow bores or lumens 30, 32. The central lumen 30 is surrounded by six smaller peripheral lumens 32 arranged in an evenly distributed array that is concentric with the central lumen and with the catheter body. The central lumen is occupied by a primary cable 34 or other conduit that serves as a connection between the connector 22 and the primary transducer. The cable may be of any appropriate type, whether a multiple-wire bundle for carrying high speed signals to and from the transducer, or fiber optics for carrying images or illumination, or wire with high current capacity for carrying electricity for cauterization or ablation, or any combination of these or other conventional catheterized elements.

One or more of the peripheral lumens about the array may carry high-strength wires that extend from a control mechanism (not shown) to the catheter's free end for "steering" the catheter by inducing bending in response to tension or compression of the wire. One of the illustrated lumens 32 remains empty.

Four of the peripheral lumens are each occupied by a coaxial cable 36. Each cable 36 has a central conductor 40 surrounded by a dielectric layer 42, which is wrapped by a conductive shield 44, which is covered by a jacket 46. In alternative embodiments, the cable may have more than one independent shield, or may be a shielded or unshielded twisted pair, or any other cable having at least two separate conductors. At the location of the coil to which the cable is connected, the coaxial cable is stripped to provide an exposed central conductor at the end, with exposed dielectric adjacent, exposed shield adjacent to that, and the remaining portion with jacket intact. This provides exposed spaced-apart contact areas to which the coil leads connect, as will be discussed below.

At one location for each lumen carrying a cable 36, and at the position of the coil to which the cable is connected, the catheter defines a pair of apertures 50, 52. The apertures provide communication with the lumen 32, and are aligned with the axis of the catheter, so that they are spaced apart along the length of the catheter. Each lumen defines one pair of apertures, and the pair for each lumen is positioned at the different locations along the length of the catheter to correspond with the different coil locations. Each cable is positioned so that the exposed shield 44 is aligned with the first aperture 50, and with the exposed central conductor 40 aligned with the second aperture 52.

Each coil 26 is a closely-wound helix, preferably in a single layer to minimize overall girth and bulk of the catheter at the coil location. The coil is wound at the location between the apertures 50, 52, so that it is fully supported. The coil has opposed end leads 54, 56 that extend in opposite directions, generally parallel to the length of the catheter, aligned with the respective apertures 50, 52. Each lead is formed to extend down into the associated aperture, and parallel against the shield 44, or conductor 40, to enable them to be electrically connected.

In this configuration, only one conductor passes through the coil, and all connections are made below the surface of the catheter, so that the only effect the cable has on the bulk is in the thickness of the coil itself. The coil is positioned between the exposed conductors 40, 44 of the cable, entirely over the exposed dielectric section 42. Because the coil surrounds the entire catheter, it also surrounds the central cable 34, and any other cables that are extending to coils located farther toward the free end.

The advantages of bulk reduction are further enhanced by the configuration in which the coaxial cables are stripped. In a conventional approach for connection to coil leads on the same side of the coil, the shield is cut to the same length as the central conductor, and is gathered at one side of the central conductor. This creates significant bulk because of the bunched shield, and because it is adjacent to the connection for the central conductor. In contrast, the preferred embodiment separates these connections to different axial locations, and maintains the shield in its slim original coaxial condition.

In an alternative embodiment in which bulk is less of a concern, the coil may be wound in more than one layer. If wound in an odd number of layers, the leads may still extend in opposite directions for connection as shown. If wound in two or another even number of layers, the leads may extend the same direction, requiring a single aperture on that side of the coil, with adequate space to expose both the central conductor and the shield, so that each lead may be soldered to the respective conductor.

In further alternative embodiments, there may be any different number of lumens and coils. One alternative may employ only a single lumen centered in a small diameter catheter, for use with only a single coil.

In the preferred embodiment, the catheter is formed of a low-friction, flexible biocompatible material such as ethylene/tetrafluoroethylene copolymer (ETFE), and has a length of 1.0 to 1.2 m (40 to 48 in), and a diameter of 3.18 mm (0.125 in). The peripheral lumens have a diameter of 0.31 mm (0.012 in). The apertures are each 0.31 mm (0.012 in) wide by 0.51 mm (0.020 in) long. The coils are formed of 36 to 48 gauge wire, and are wrapped 5 to 25 times about the catheter. The cable central conductor is 40 to 52 gauge wire. The dielectric has a diameter of about three times the central wire diameter, and the shield is formed of a wrap of 48 to 56 gauge wire, and the jacket thickness is 0.013 mm (0.0005 in) for an overall cable diameter of about 0.25 mm (0.010 in).

While the above is discussed in terms of preferred and alternative embodiments, the invention is not intended to be so limited.

What is claimed is:

1. A cable assembly comprising:
    an elongated catheter having an exterior and defining a lumen;
    a cable within the lumen and having at least first and second electrically independent conductors;
    a first electrical component connected to the catheter and having a first lead extending in a first direction toward a first end of the catheter and a second lead extending in a second direction, different from the first direction, toward a second end, different from the first end, of the catheter, the first component being a coil surrounding the exterior of the entire catheter;
    the first lead connected to the first conductor at a first connection;
    the second lead connected to the second conductor at a second connection;
    the first and second connections being spaced apart along the length of the catheter; and
    the first component being positioned at an intermediate location between the first and second connections.

2. The cable assembly of claim 1 wherein the first conductor is a central conductor of a coaxial cable, and the second conductor is a shield surrounding the first conductor.

3. The cable assembly of claim 2 wherein the cable is stripped to provide:
    a first section comprising an exposed free end portion of the central conductor,
    an adjacent second section comprising the central conductor surrounded by dielectric,
    an adjacent third section comprising dielectric surrounded by exposed shield, and
    an adjacent fourth section comprising shield surrounded by an insulating sheath.

4. The cable assembly of claim 3 wherein the first component is aligned with the second section.

5. The cable assembly of claim 1 including a second cable connected to a second component and connected to the catheter, the second component being located at a position spaced apart from the first component along the length of the catheter.

6. The cable assembly of claim 5 wherein the catheter defines multiple lumens, and wherein the first and second cables are received in different lumens.

7. A cable assembly comprising:
    an elongated catheter having an exterior, defining a lumen and having a free end and an opposed connection end;
    a first electrical component connected to the catheter proximate the free end and having a first lead and second lead, the first component being a coil surrounding the exterior of the entire catheter;
    a first cable within the lumen, having at least first and second electrically independent conductors, and extending from the connection end of the catheter to the component;
    the first lead of the first component extending toward the free end of the catheter; and
    the second lead of the first component extending toward the connection end of the catheter.

8. The cable assembly of claim 7 wherein the first lead is connected to the first conductor at a first connection, the second lead is connected to the second conductor at a second connection, the first and second connections are spaced apart along the length of the catheter, and the component is positioned at an intermediate location between the first and second connections.

9. The cable assembly of claim 7 wherein the first conductor is a central conductor of a coaxial cable, and the second conductor is a shield surrounding the first conductor.

10. The cable assembly of claim 9 wherein the cable is stripped to provide:

a first section comprising an exposed free end portion of the central conductor, an adjacent second section comprising the central conductor surrounded by dielectric, an adjacent third section comprising dielectric surrounded by exposed shield, and an adjacent fourth section comprising shield surrounded by an insulating sheath.

11. The cable assembly of claim 10 wherein the component is aligned with the second section.

12. The cable assembly of claim 7 including a second cable connected to a second component and connected to the catheter, the second component being located at a position spaced apart from the first component along the length of the catheter.

13. The cable assembly of claim 12 wherein the catheter defines multiple lumens, and wherein the first and second cables are received in different lumens.

14. A cable assembly comprising:

an elongated catheter defining a lumen;

a cable within the lumen having an exterior and having at least first and second electrically independent conductors;

a first coil defining a bore surrounding the exterior of the entire catheter and having a first lead and second lead;

the first lead connected to the first conductor at a first connection;

the second lead connected to the second conductor, different from the first conductor, at a second connection, different from the first connection; and only one of the first and second leads passing through the bore.

15. The cable assembly of claim 14 wherein the first conductor is a central conductor of a coaxial cable, and the second conductor is a shield surrounding the first conductor.

16. The cable assembly of claim 15 wherein the cable is stripped to provide:

a first section comprising an exposed free end portion of the central conductor, an adjacent second section comprising the central conductor surrounded by dielectric, an adjacent third section comprising dielectric surrounded by exposed shield, an adjacent fourth section comprising shield surrounded by an insulating sheath; and wherein the coil is aligned with the second section.

17. The cable assembly of claim 14 including a second cable connected to a second coil and connected to the catheter, the second coil being located at a position spaced apart from the first coil along the length of the catheter, and the second cable passing through the bore defined by the first coil.

* * * * *